United States Patent [19]
Bone et al.

[11] Patent Number: 5,690,696
[45] Date of Patent: Nov. 25, 1997

[54] COMBINATIONS OF TWO PARA-PHENYLENEDIAMINE OXIDATION BASES AND A META-PHENYLENEDIAMINE COUPLER FOR THE OXIDATION DYEING OF KERATINOUS FIBERS

[75] Inventors: Eric Bone, Clichy; Roland De La Mettrie, Le Vesinet, both of France

[73] Assignee: L'Oreal, Paris, France

[21] Appl. No.: 588,726

[22] Filed: Jan. 19, 1996

[30] Foreign Application Priority Data

Jan. 19, 1995 [FR] France ................................. 95 00587

[51] Int. Cl.⁶ ............................................. A61K 7/13
[52] U.S. Cl. ........................... 8/411; 8/407; 8/408; 8/410; 8/416
[58] Field of Search ........................ 8/406, 407, 408, 8/410, 411, 416

[56] References Cited

U.S. PATENT DOCUMENTS

| | | | |
|---|---|---|---|
| 3,884,627 | 5/1975 | Brody et al. | 8/411 |
| 3,970,423 | 7/1976 | Brody et al. | 8/10.2 |
| 4,125,367 | 11/1978 | Bugaut et al. | 8/11 |
| 4,259,261 | 3/1981 | Bugaut et al. | 564/99 |
| 4,329,504 | 5/1982 | Bugaut et al. | 564/443 |
| 4,333,730 | 6/1982 | Bugaut et al. | 8/410 |
| 4,361,421 | 11/1982 | Bugaut et al. | 8/410 |
| 4,420,637 | 12/1983 | Bugaut et al. | 8/410 |
| 4,556,876 | 12/1985 | Brown et al. | 8/411 |
| 4,854,935 | 8/1989 | Clausen et al. | 8/411 |

FOREIGN PATENT DOCUMENTS

| | | |
|---|---|---|
| 2 156 527 | 6/1973 | France . |
| 2 362 116 | 3/1978 | France . |
| 2 054 665 | 2/1981 | United Kingdom . |
| 1597034 | 9/1981 | United Kingdom . |
| 2078747 | 1/1982 | United Kingdom . |
| A2180215 | 3/1987 | United Kingdom . |
| 93 10744 | 6/1993 | WIPO . |

*Primary Examiner*—Paul Lieberman
*Assistant Examiner*—Caroline L. Dusheck
*Attorney, Agent, or Firm*—Finnegan, Henderson, Farabow, Garrett & Dunner

[57] ABSTRACT

A composition for the oxidation dyeing of keratinous fibres, especially human keratinous fibres such as hair, which comprises para-phenylenediamine and/or 2-methyl-para-phenylenediamine and/or acid addition salts thereof in combination with at least one appropriately selected meta-phenylenediamine derivative and/or acid addition salts thereof and at least one appropriately selected tertiary para-phenylenediamine derivative, and/or acid addition salts thereof, and to the dyeing process using this composition.

26 Claims, No Drawings

COMBINATIONS OF TWO PARA-PHENYLENEDIAMINE OXIDATION BASES AND A META-PHENYLENEDIAMINE COUPLER FOR THE OXIDATION DYEING OF KERATINOUS FIBERS

The invention relates to a composition for the oxidation dyeing of keratinous fibres, especially human keratinous fibres such as hair, that comprises para-phenylenediamine and/or 2-methyl-para-phenylenediamine in combination with at least one appropriately selected meta-phenylenediamine derivative and at least one appropriately selected tertiary para-phenylenediamine derivative, and to the dyeing process using this composition.

It is known to dye keratinous fibres, and in particular human hair, with dyeing compositions containing oxidation dye precursors, in particular ortho- or para-phenylenediamines or ortho- or para-aminophenols, which are generally referred to as oxidation bases. Oxidation dye precursors, or oxidation bases, are colourless or slightly coloured compounds that, in combination with oxidizing products, are able by a process of oxidative condensation to give rise to coloured compounds and dyes.

It is also known that is possible to vary the shades obtained with these oxidation bases by combining them with couplers or dye modifiers, the latter being chosen in particular from aromatic meta-diamines, meta-amino phenols and meta-diphenols.

The variety of modules that are employed as oxidation bases and as couplers makes it possible to obtain a rich palette of colours.

The so-called permanent colouration that is obtained by virtue of these oxidation dyes must, moreover, satisfy a certain number of demands. It must not be toxic, and it must make it possible to obtain shades of the desired intensity. Also it must be of good persistence vis-a-vis external agents (light, inclement weather, washing, perming, perspiration, rubbing). The dyes must also make it possible to colour white hair.

Finally, the dyes must be as unselective as possible. In other words, they must make it possible to obtain minimal deviations in colouring right along a single keratinous fibre, which can in fact be of different sensitivity (i.e., damaged) between its end and its root.

There have already been proposals, in particular in French Patent FR-2 362 116, for compositions for the oxidation dyeing of keratinous fibres that comprise at least one meta-phenylenediamine derivative as coupler in combination with at least one oxidation dye precursor. The colourations obtained with these compositions are not, however, entirely satisfactory, especially as regards the persistence of these colourations vis-a-vis the various aggressive agents to which the hair can be subject, in particular shampoos and light.

The aim of the present invention is to provide novel compositions for the oxidation dyeing of keratinous fibres, and especially of human keratinous fibres such as hair, having very good dyeing properties.

The Inventors have discovered that it is possible to obtain novel dyes that are particularly resistant, and that give rise to intense colourations of low selectivity, by combining:

para-phenylenediamine and/or 2-methyl-para-phenylenediamine and/or one of their addition salts with an acid, at least one specific meta-phenylenediamine derivative of formula (I) defined below, and at least one specific tertiary para-phenylenediamine derivative of formula (II) defined below.

It is this discovery which forms the basis of the present invention.

A first subject of the invention is therefore a composition for the oxidation dyeing of keratinous fibres, and especially of human keratinous fibres such as hair, characterized in that it comprises, in a medium appropriate for dyeing:

at least one first oxidation base selected from para-phenylenediamine, 2-methyl-para-phenylenediamine, and their addition salts with an acid, at least one coupler selected from meta-phenylenediamine compounds of formula (I) below:

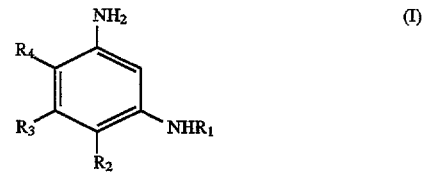

in which:

$R_1$ represents a hydrogen atom or a $C_1$–$C_4$ alkyl, $C_1$–$C_4$ monohydroxyalkyl, or $C_2$–$C_4$ polyhydroxyalkyl radical;

$R_2$ and $R_3$, which are identical or different, represent a hydrogen atom or a $C_1$–$C_4$ alkyl or $C_1$–$C_4$ hydroxyalkoxy radical;

$R_4$ represents a $C_1$–$C_4$ alkoxy, $C_1$–$C_4$ aminoalkoxy, $C_1$–$C_4$ monohydroxyalkoxy, or $C_2$–$C_4$ polyhydroxyalkoxy radical or a 2,4-diaminophenoxy $C_1$–$C_4$ alkoxy radical, with the proviso that, when $R_1$ denotes a hydrogen atom, $R_2$ and $R_4$ do not simultaneously denote a β-hydroxyethyloxy radical, and that, when $R_1$, $R_2$ and $R_3$ simultaneously denote a hydrogen atom, $R_4$ is other than methoxy, and their addition salts with an acid, and at least one second oxidation base selected from tertiary para-phenylenediamine derivatives of formula (II) below:

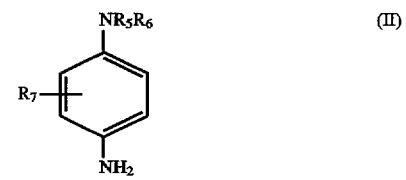

in which:

$R_5$ represents a $C_1$–$C_4$ alkyl, $C_1$–$C_4$ monohydroxyalkyl or $C_2$–$C_4$ polyhydroxyalkyl radical;

$R_6$ represents a $C_1$–$C_4$ monohydroxyalkyl or $C_2C_4$ polyhydroxyalkyl radical;

$R_7$ represents a hydrogen atom, a $C_1$–$C_4$ alkyl or $C_1$–$C_4$ alkoxy radical or a halogen atom, and their addition salts with acid.

The colourations obtained with the above compositions are of good tinctorial strength and have excellent properties of resistance both to atmospheric agents, such as light and inclement weather, and to perspiration and the various treatments to which the hair may be subject (shampooings, perms). These properties are particularly noteworthy, especially as regards the resistance of the colourations obtained to shampooing and to light.

Another subject of the invention is a process for the oxidation dyeing of keratinous fibres using this composition.

The addition salts with an acid that can be used within the context of the dyeing compositions of the invention can in particular be chosen from hydrochlorides, hydrobromides, sulphates, and tartrates.

Among the meta-phenylenediamine derivatives of formula (I) above, more particular mention may be made of 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxypropyl-oxy)benzene, 2,4-diamino-1-(β-hydroxyethyloxy)benzene, 2-amino-4-N-(β-hydroxyethyl)amino-1-methoxybenzene and their addition salts with an acid.

Among the tertiary para-phenylenediamine derivatives of formula (II) above, more particular mention may be made of 1-(N-ethyl-N'-β-hydroxyethyl)-amino-4-aminobenzene, 1-N,N'-bis(β-hydroxyethyl)amino-4-aminobenzene, 1-N,N'-bis(β,γ-dihydroxypropyl)amino-4-aminobenzene and their addition salts with an acid.

The para-phenylenediamine and/or the 2-methyl-para-phenylenediamine and/or the addition salt or salts of these compounds with an acid preferably represent from approximately 0.0005 to 10% by weight of the total weight of the dyeing composition, and still more preferably from approximately 0.05 to 7% by weight.

The meta-phenylenediamine derivative or derivatives of formula (I) which are in accordance with the invention preferably represent from approximately 0.0001 to 5% by weight of the total weight of the dyeing composition, and still more preferably from approximately 0.005 to 3% by weight.

The tertiary para-phenylenediamine derivative or derivatives of formula (II) which are in accordance with the invention preferably represent from approximately 0.0005 to 10% by weight of the total weight of the dyeing composition, and still more preferably from approximately 0.05 to 7% by weight.

The medium appropriate for dyeing (or vehicle) comprises in general water or a mixture of water and at least one organic solvent in order to solubilize those compounds which would not be sufficiently soluble in water. As organic solvent mention may be made for example of lower $C_1$–$C_4$ alkanols, such as ethanol and isopropanol; glycerol; glycols and glycol ethers, such as 2-butoxyethanol, propylene glycol, diethylene glycol monoethyl ether and monomethyl ether; and also aromatic alcohols such as benzyl alcohol or phenoxyethanol, similar solvents and mixtures thereof.

The solvents may be present in proportions that are preferably from approximately 1 to 40% by weight relative to the total weight of the dyeing composition, and still more preferably from approximately 5 to 30% by weight.

The pH of the dyeing composition as defined above generally ranges from 2 to 12. It can be adjusted to the desired value using acidifying or basifying agents that are customarily used in the dyeing of keratinous fibres.

Among acidifying agents, mention may be made, by way of example, of mineral or organic acids, such as hydrochloric acid, orthophosphoric acid, carboxylic acids such as tartaric acid, citric acid and lactic acid, and sulphonic acids.

Among the basifying agents, mention may be made, by way of example, of aqueous ammonia, alkali metal carbonates, alkanol amines such as mono-, di- and triethanol amines and derivatives thereof, sodium hydroxide or potassium hydroxide, and compounds of formula (III) below:

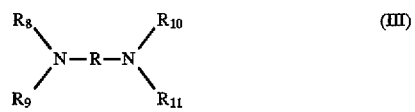

in which R is a propylene radical which is optionally substituted with a hydroxyl group or a $C_1$–$C_4$ alkyl radical; $R_8$, $R_9$, $R_{10}$ and $R_{11}$, which are identical or different, represent a hydrogen atom or a $C_1$–$C_4$ alkyl or $C_1$–$C_4$ hydroxyalkyl radical.

The dyeing composition in accordance with the invention may also contain, in addition to the dyes defined above, other oxidation bases and/or other couplers and/or direct dyes, especially for modifying shades or for enriching them with glints.

The dyeing composition according to the invention may also comprise various adjuvants which are conventionally used in hair-dyeing compositions, such as anionic, cationic, nonionic, amphoteric or zwitterionic surfactants or mixtures thereof, inorganic or organic thickeners, antioxidants, penetration agents, sequestering agents, fragrances, buffers, dispersants, silicones, film-formers, preservatives, opacifying agents, and conditioners such as silicones.

The dyeing composition according to the invention may be presented in various forms, such as in the form of liquids, creams or gels, or in any other form that is suitable for carrying out dyeing of keratinous fibres, and especially human hair.

Another subject of the invention is a process for dyeing keratinous fibres, and especially human keratinous fibres such as hair, using the dyeing composition as defined above.

According to this process, the dyeing composition as defined above is applied to the fibres that are to be coloured, the colour being revealed at an acid, neutral or alkaline pH with the aid of an oxidizing agent that is added at the time of use to the dyeing composition or that is present in an oxidizing composition applied separately at the same time or sequentially.

According to a particularly preferred embodiment of the dyeing process of the present invention, the dyeing composition described above is mixed at the time of use with an oxidizing composition that contains, in a medium appropriate for dyeing, at least one oxidizing agent that is present in a sufficient quantity to develop a colouration. The mixture obtained is subsequently applied to the keratinous fibres and is preferably left to act for from approximately 3 to 40 minutes, more preferably from approximately 5 to 30 minutes, after which the fibres are rinsed, shampooed, rinsed again, and dried.

The oxidizing agent present in the oxidizing composition as defined above can be chosen from the oxidizing agents that are conventionally used for the oxidation dyeing of keratinous fibres, among which may be mentioned hydrogen peroxide, urea peroxide, alkali metal bromates, and per salts such as perborates and persulphates. Hydrogen peroxide is particularly preferred.

The pH of the oxidizing composition containing the oxidizing agent as defined above is such that, after mixing with the dyeing composition, the pH of the resulting composition that is applied to the keratinous fibres preferably ranges from about 2 to 12, and still more preferably from 5 to 11. It is adjusted to the desired value by means of acidifying or basifying agents that are customarily used in the dyeing of keratinous fibres, such as those defined above.

The oxidizing composition as defined above can also contain various adjuvants that are conventionally used in compositions for the dyeing of hair, such as those defined above.

The composition that is ultimately applied to the keratinous fibres can be presented in various forms, such as in the form of liquids, creams or gels, or in any other form appropriate for dyeing keratinous fibres, and especially human hair.

Another subject of the invention is a multi-compartment device or dyeing kit, or any other packaging system having a plurality of compartments, of which a first compartment contains the dyeing composition as defined above and a second compartment contains the oxidizing composition as defined above. These devices may be equipped with a means enabling the desired mixture to be applied to the hair, such as the devices described in the Applicant's patent FR-2 586 913, which is incorporated herein by reference.

The invention will now be described in greater detail by means of the following examples, which are given solely by way of illustration and in no way limit the invention.

EXAMPLES

Examples 1 to 3

The following dyeing compositions in accordance with the invention were prepared (contents in grams):

| EXAMPLE | 1 | 2 | 3 |
|---|---|---|---|
| Para-phenylenediamine | 0.7 | | 0.2 |
| 2-Methyl-para-phenylenediamine | | 0.2 | |
| 2,4-Diamino-1-(β-hydroxy-ethyloxy)benzene dihydrochloride | 0.08 | 0.05 | |
| 2-Amino-4-N-(β-hydroxy-ethyl)amino-1-methoxybenzene | | | 0.1 |
| 1-N,N'-Bis(β-hydroxyethyl)amino-4-aminobenzene sulphate | 0.15 | 0.3 | 0.1 |
| Resorcinol | 0.5 | 0.4 | 0.35 |
| Common dye vehicle (*) | (*) | (*) | (*) |
| Water qs | 100 g | 100 g | 100 g |

(*)Common dye vehicle:

| | |
|---|---|
| Oleyl alcohol, polyglycerolated with 2 mol of glycerol | 4.0 g |
| Oleyl alcohol, polyglycerolated with 4 mol of glycerol, containing 78% of active substances (AS) | 5.69 g AS |
| Oleic acid | 3.0 g |
| Oleylamine with 2 mol of ethylene oxide, sold under the trade name ETHOMEEN 012 by the company AKZO | 7.0 g |
| Diethylaminopropyl laurylamino-succinamate, sodium salt, containing 55% AS | 3.0 g AS |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% AS | 0.455 g AS |
| Ammonium acetate | 0.8 g |
| Antioxidant, sequestering agent | qs |
| Fragrance, preservative | qs |
| Aqueous ammonia containing 20% $NH_3$ | 10.2 g |

At the time of use, each dyeing composition was mixed with an equal quantity of an oxidizing composition consisting of 20-volume hydrogen peroxide solution (6% by weight) having a pH of approximately 3.

Each mixture obtained had a pH of approximately 10.2 and was applied for 30 minutes to locks of natural grey hair containing 90% white hairs. The locks of hair were subsequently rinsed, washed with a standard shampoo, and then dried.

The locks of hair were dyed in the shades indicated in the table below:

| EXAMPLE | SHADE ON NATURAL HAIR |
|---|---|
| 1 | ash chestnut |
| 2 | dark blond |
| 3 | ash blond |

Examples 4 to 6

The following dyeing compositions were prepared:

| EXAMPLE | 4() | 5() | 6(***) |
|---|---|---|---|
| Para-phenylenediamine (mol) | $3.10^{-3}$ | | $2.5 \times 10^{-3}$ |
| 2,4-Diamino-1-(β-hydroxy ethyloxy)benzene dihydrochloride (mol) | $3.10^{-3}$ | $3.10^{-3}$ | $0.5 \times 10^{-3}$ |
| 1-N,N'-bis(β-hydroxy-ethyl)amino-4-aminobenzene sulphate (mol) | | $3.10^{-3}$ | $3.10^{-3}$ |
| Common dye vehicle (*) | (*) | (*) | (*) |
| Water qs | 100 g | 100 g | 100 g |

(*): see earlier
(**): examples which are not part of the invention
(***): example which is part of the invention Each dyeing composition comprises in total $6 \times 10^{-3}$ mol of dyes.

At the time of use, each dyeing composition was mixed with an equal quantity of an oxidizing composition consisting of 20-volume hydrogen peroxide solution (6% by weight) having a pH of approximately 3.

Each mixture obtained had a pH of approximately 10.2, and was applied for 30 minutes to locks of permed grey hair containing 90% white hairs. The locks of hair were subsequently rinsed, washed with a standard shampoo and then dried.

The colour of the locks was subsequently evaluated in the MUNSELL system by means of a MINOLTA CM 2002 colorimeter.

According to the MUNSELL notation, a colour is defined by the term H V/C in which the three parameters denote, respectively, the shade or hue (H), the intensity or value (V), and the purity or chromaticity (C), the oblique bar in this term being simply a convention and not indicating a ratio.

The locks of hair thus dyed were subsequently subjected to a wash resistance test (Ahiba-Texomat) machine.

For this purpose, the locks of hair were placed in a basket which was immersed in a solution of a standard shampoo. The basket was subjected to an up-and-down movement of variable frequency and to a rotational movement, which movements reproduce the action of manual rubbing, which gives rise to the formation of foam.

After 3 minutes of testing, the locks were withdrawn, rinsed, and then dried. The dyed locks were subjected to 8 consecutive shampooing tests.

The colour of the locks was subsequently evaluated again in the MUNSELL system using a MINOLTA CM 2002 colorimeter.

The difference between the colour of the lock before shampooing and the colour of the lock after shampooing was calculated by applying the NICKERSON formula:

$$\Delta E = 0.4\, C o \Delta H + 6 \Delta V + 3 \Delta C,$$

as described for example in "Couleur, Industrie et Technique"; pages 14–17; vol. No. 5; 1978.

In this formula, ΔE represents the difference in colour between two locks, ΔH, ΔV and ΔC represent the change in absolute value of the parameters H, V and C, and Co represents the purity of the lock relative to which the difference in colour is to be evaluated. The results are given in the table below:

| EX-AMPLE | Hair colour before shampooing | Hair colour after shampooing | Impairment of colour | | | |
|---|---|---|---|---|---|---|
| | | | ΔH | ΔV | ΔC | ΔE |
| 4 | 8.55 PB 0.3/1.7 | 9.5 PB 1.9/2.1 | 0.95 | 1.6 | 0.4 | 11.5 |
| 5 | 6.75 PB 0.3/3.4 | 1.25 PB 1.6/4.1 | 5.5 | 1.3 | 0.7 | 17.4 |
| 6 | 7.95 PB 0.3/1.6 | 7.0 PB 0.9/2.8 | 0.95 | 0.6 | 1.2 | 7.8 |

These results show that a composition of Example 6, which is in accordance with the invention, i.e., that comprises para-phenylenediamine, a meta-phenylenediamine derivative of formula (I) according to the invention, and a tertiary para-phenylenediamine derivative of formula (II) in accordance with the invention, leads to a colouration that is much more resistant to shampooing than the colourations obtained with the compositions of Examples 4 and 5, which are not part of the invention since each of them contains only two of the three compounds above.

We claim:

1. A composition for the oxidation dyeing of keratinous fibres comprising, in a medium appropriate for dyeing:

from 0.0005 to 10% by weight of the total weight of the dyeing composition of at least one first oxidation base selected from para-phenylenediamine, an acid addition salt thereof, 2-methyl-para-phenylenediamine, and an acid addition salt thereof;

from 0.0001 to 5% by weight of the total weight of the dyeing composition of at least one coupler selected from meta-phenylenediamine compounds of formula (I) below:

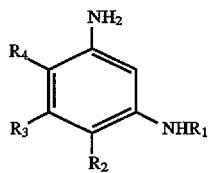

in which:

$R_1$ represents a hydrogen atom or a $C_1$–$C_4$ alkyl, $C_1$–$C_4$ monohydroxyalkyl or $C_2$–$C_4$ polyhydroxyalkyl radical;

$R_2$ and $R_3$, which are identical or different, represent a hydrogen atom or a $C_1$–$C_4$ alkyl or $C_1$–$C_4$ hydroxyalkoxy radical;

$R_4$ represents a $C_1$–$C_4$ alkoxy, $C_1$–$C_4$ aminoalkoxy, $C_1$–$C_4$ monohydroxyalkoxy or $C_2$–$C_4$ polyhydroxyalkoxy radical or a 2,4-diaminophenoxy $C_1$–$C_4$ alkoxy radical, with the proviso that, when $R_1$ denotes a hydrogen atom, $R_2$ and $R_4$ do not simultaneously denote a β-hydroxyethyloxy radical, and that, when $R_1$, $R_2$ and $R_3$ simultaneously denote a hydrogen atom, $R_4$ is other than methoxy, and acid addition salts of the compounds of formula (I), and from 0.0005 to 10% by weight of the total weight of the dyeing composition of at least one second oxidation base selected from para-phenylenediamine compounds of formula (II) below:

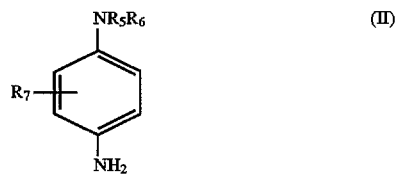

in which:

$R_5$ represents a $C_1$–$C_4$ alkyl, $C_1$–$C_4$ monohydroxyalkyl or $C_2$$C_4$ polyhydroxyalkyl radical;

$R_6$ represents a $C_1$–$C_4$ monohydroxyalkyl or $C_2$–$C_4$ polyhydroxyalkyl radical;

$R_7$ represents a hydrogen atom, a $C_1$–$C_4$ alkyl or $C_1$–$C_4$ alkoxy radical or a halogen atom, and acid addition salts of the compounds of formula (II).

2. A composition according to claim 1, wherein the keratinous fibres are human keratinous fibres.

3. A composition according to claim 2, wherein the human keratinous fibres are hair.

4. A composition according to claim 1, wherein said acid addition salts are selected from hydrochlorides, hydrobromides, sulphates and tartrates.

5. A composition according to claim 1, wherein the meta-phenylenediamine compounds of formula (I) are selected from 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diamino-phenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene, 2-amino-4-N-(β-hydroxyethyl)amino-1-methoxybenzene and acid addition salts of said compounds.

6. A composition according to claim 1, wherein the para-phenylenediamine compounds of formula (II) are selected from 1-(N-ethyl-N'-β-hydroxyethyl)amino-4-aminobenzene, 1-N,N'-bis(β-hydroxyethyl)amino-4-aminobenzene, 1-N,N'-bis(β,γ-dihydroxypropyl)amino-4-aminobenzene and acid addition salts of said compounds.

7. A composition according to claim 1, wherein said at least one first oxidation base selected from para-phenylenediamine, an acid addition salt thereof, 2-methyl-para-phenylenediamine, and an acid addition salt thereof represents from 0.05 to 7% by weight of the total weight of the dyeing composition.

8. A composition according to claim 1, wherein said at least one coupler selected from meta-phenylenediamine compounds of formula (I) and acid addition salts thereof represents from 0.005 to 3% by weight of the total weight of the dyeing composition.

9. A composition according to claim 1, wherein said at least one second oxidation base selected from para-phenylenediamine compounds of formula (II) and acid addition salts thereof represents from 0.05 to 7% by weight of the total weight of the dyeing composition.

10. A composition according to claim 1, wherein said medium appropriate for dyeing comprises water or a mixture of water and at least one organic solvent selected from $C_1$–$C_4$ lower alkanols, glycerol, glycols and glycol ethers, and aromatic alcohols.

11. A composition according to claim 1, having a pH ranging from 2 to 12.

12. A composition according to claim 1, further comprising at least one oxidation base other than those selected from para-phenylenediamine, acid addition salts thereof, 2-methyl-para-phenylenediamine, acid addition salts thereof, para-phenylenediamine compounds of formula (II) and acid addition salts thereof.

13. A composition according to claim 12, further comprising at least one coupler other than those selected from meta-phenylenediamine compounds of formula (I) and acid addition salts thereof.

14. A composition according to claim 13, further comprising at least one direct dye.

15. A composition according to claim 12, further comprising at least one direct dye.

16. A composition according to claim 1, further comprising at least one coupler other than those selected from meta-phenylenediamine compounds of formula (I) and acid addition salts thereof.

17. A composition according to claim 16, further comprising at least one direct dye.

18. A composition according to claim 1, further comprising at least one direct dye.

19. A method for dyeing keratinous fibres comprising the step of applying a dyeing composition as defined in claim 1 and an oxidizing agent to said fibres; or the step of applying a dyeing composition as defined in claim 1 and an oxidizing composition to said fibres, said oxidizing composition containing an oxidizing agent and said oxidizing composition being applied separately from said dyeing composition to said fibres either at the same time as said dyeing composition is applied to said fibres or sequentially, and whereby in either step, a colour is developed at an acid, neutral or alkaline pH.

20. A method according to claim 19, wherein the keratinous fibres are human keratinous fibres.

21. A method according to claim 20, wherein the human keratinous fibres are hair.

22. A method according to claim 19, wherein the oxidizing agent that is present in the oxidizing composition is selected from hydrogen peroxide, urea peroxide, alkali metal bromates, and per salts.

23. A method according to claim 22, wherein the per salts are selected from perborates and persulphates.

24. A multi-compartment device or dyeing kit comprising a plurality of compartments, including a first compartment containing a dyeing composition as defined in claim 1 and a second compartment containing an oxidizing composition comprising an oxidizing agent.

25. A multi-compartment device or dyeing kit according to claim 21 wherein said oxidizing agent is selected from hydrogen peroxide, urea peroxide, alkali metal bromates, and per salts.

26. A multi-compartment device or dyeing kit according to claim 25, wherein the per salts are selected from perborates and persulphates.

* * * * *